(12) United States Patent
Downie et al.

(10) Patent No.: US 9,255,870 B2
(45) Date of Patent: Feb. 9, 2016

(54) METHOD OF AND APPARATUS FOR MEASURING THE TRUE CONTENTS OF A CYLINDER OF GAS UNDER PRESSURE

(75) Inventors: Neil Alexander Downie, Hampshire (GB); Marcel Behrens, Vilvoorde (BE); Lateef Olusegun Adigun Obadun, Berkshire (GB)

(73) Assignee: AIR PRODUCTS AND CHEMICALS, INC., Allentown, PA (US)

( * ) Notice: Subject to any disclaimer, the term of this patent is extended or adjusted under 35 U.S.C. 154(b) by 351 days.

(21) Appl. No.: 13/989,212

(22) PCT Filed: Nov. 28, 2011

(86) PCT No.: PCT/EP2011/071198
§ 371 (c)(1),
(2), (4) Date: Jul. 23, 2013

(87) PCT Pub. No.: WO2012/072588
PCT Pub. Date: Jun. 7, 2012

(65) Prior Publication Data
US 2013/0306650 A1    Nov. 21, 2013

(30) Foreign Application Priority Data

Nov. 29, 2010 (EP) .................................. 10192962

(51) Int. Cl.
| | | |
|---|---|---|
| G01G 9/00 | (2006.01) | |
| G01N 9/36 | (2006.01) | |
| F17C 13/02 | (2006.01) | |
| G01F 1/86 | (2006.01) | |
| G01F 15/06 | (2006.01) | |
| G01G 3/16 | (2006.01) | |
| G01G 17/04 | (2006.01) | |
| G01N 9/00 | (2006.01) | |

(52) U.S. Cl.
CPC ........ *G01N 9/36* (2013.01); *F17C 13/02* (2013.01); *F17C 13/023* (2013.01); *G01F 1/86* (2013.01);

(Continued)

(58) Field of Classification Search
None
See application file for complete search history.

(56) References Cited

U.S. PATENT DOCUMENTS

| | | | | |
|---|---|---|---|---|
| 3,420,092 A | * | 1/1969 | Dorsch | ................ G01L 9/0008 |
| | | | | 73/24.05 |
| 5,421,190 A | | 6/1995 | Brandle et al. | |

(Continued)

FOREIGN PATENT DOCUMENTS

| | | |
|---|---|---|
| DE | 19945881 A1 | 4/2000 |
| DE | 10232823 A | 11/2003 |

(Continued)

OTHER PUBLICATIONS

European Patent Office, International Search Report for PCT Application No. PCT/EP2011/071198, mailed Aug. 3, 2012.

*Primary Examiner* — Andre Allen
(74) *Attorney, Agent, or Firm* — Larry S. Zelson

(57) ABSTRACT

There is provided a method of, and apparatus for, measuring the mass of a gas under pressure using a piezoelectric oscillator. The gas is contained within a pressure vessel (100) having a fixed internal volume (V) and the piezoelectric oscillator (202) is immersed in the gas within the pressure vessel (100). The method comprises: a) utilizing said piezoelectric oscillator (202) to measure the density of the gas within the high-pressure vessel (100); b) determining, from the density measurement and from the internal volume (V) of said pressure vessel, the mass of the gas within the pressure vessel (100). By providing such a method, the true contents (i.e. mass) of fluid in a pressure vessel such as a cylinder can be measured directly without the need to compensate for factors such as temperature or compressibility. This allows a determination of mass through direct derivation from the density of the gas in the cylinder, reducing the need for additional sensors or complex calculations to be performed.

11 Claims, 12 Drawing Sheets

(52) U.S. Cl.
CPC ............... *G01F 15/063* (2013.01); *G01G 3/16* (2013.01); *G01G 17/04* (2013.01); *G01N 9/002* (2013.01); *F17C 2250/0404* (2013.01); *F17C 2250/0421* (2013.01); *F17C 2250/0495* (2013.01); *Y10T 137/8158* (2015.04)

(56) References Cited

U.S. PATENT DOCUMENTS

| | | | |
|---|---|---|---|
| 5,455,475 A * | 10/1995 | Josse et al. | 310/316.01 |
| 6,050,598 A | 4/2000 | Upton | |
| 6,465,749 B1 * | 10/2002 | Kurz | 177/210 FP |
| 2008/0229829 A1 * | 9/2008 | Kondo | 73/579 |
| 2014/0000342 A1 * | 1/2014 | Downie | 73/24.01 |
| 2015/0096385 A1 * | 4/2015 | Downie et al. | 73/861.04 |
| 2015/0107679 A1 * | 4/2015 | Downie | 137/7 |
| 2015/0128682 A1 * | 5/2015 | Downie et al. | 73/24.01 |

FOREIGN PATENT DOCUMENTS

| | | |
|---|---|---|
| DE | 10232823 A1 | 11/2003 |
| EP | 0582045 A1 | 2/1994 |
| JP | 2000108837 A | 4/2000 |
| WO | 9940553 A | 8/1999 |
| WO | 9940553 A1 | 8/1999 |

* cited by examiner

METHOD OF AND APPARATUS FOR MEASURING THE TRUE CONTENTS OF A CYLINDER OF GAS UNDER PRESSURE

The present invention relates a method of, and apparatus for, measuring the true contents of a cylinder of gas under pressure. More particularly, the present invention relates to a method of, and apparatus for, measuring the true contents of a cylinder using a piezoelectric oscillator. The methods and apparatus described herein can be applied to systems where gas of relatively high pressure (e.g. about 10 bar or higher) are present, such as for example, the supply of gases in high pressure cylinders or manufacturing plants utilising high pressure gases. The present invention relates particularly to "clean" gases, i.e. gases with little or no impurities or contaminants such as water vapour or dust.

A compressed gas cylinder is a pressure vessel designed to contain gases at high pressures, i.e. at pressures significantly greater than atmospheric pressure. Compressed gas cylinders are used in a wide range of markets, from the low cost general industrial market, through the medical market, to higher cost applications, such as electronics manufacture utilising high purity corrosive, toxic or pyrophoric speciality gases. Commonly, pressurised gas containers comprise steel, aluminium or composites and are capable of storing compressed, liquefied or dissolved gases with a maximum filling pressure up to 450 bar g (where bar g is a measure of the pressure (in bar) above atmospheric pressure) for most gases, and up to 900 bar g for gases such as hydrogen and helium.

The present invention is particularly applicable to permanent gases. Permanent gases are gases which cannot be liquefied by pressure alone, and for example can be supplied in cylinders at pressures up to 450 bar g. Examples are Argon and Nitrogen. However, this is not to be taken as limiting and the term gas may be considered to encompass a wider range of gases, for example, both a permanent gas and a vapour of a liquefied gas. Vapours of liquefied gases are present above the liquid in a compressed gas cylinder. Gases which liquefy under pressure as they are compressed for filling into a cylinder are not permanent gases and are more accurately described as liquefied gases under pressure or as vapours of liquefied gases. As an example, nitrous oxide is supplied in a cylinder in liquid form, with an equilibrium vapour pressure of 44.4 bar g at 15° C. Such vapours are not permanent or true gases as they are liquefiable by pressure or temperature around ambient conditions.

In many instances, it is necessary to monitor the contents of a given cylinder or pressure vessel to determine the amount of gas remaining. This is particularly critical in situations such as health care applications.

It is known to calculate, in accordance with the gas laws, the true contents of a cylinder from knowledge of the pressure of gas within a cylinder. Pressure measurement is a well known art and there are a variety of devices which function to measure pressure. The most conventional type uses an elastic diaphragm equipped with strain gauge elements. However, although one of the lowest cost pressure sensors currently made, these sensors tend to be relatively large in size, and have a mechanical structure which although producible by mass-production photolithographic methods is still relatively complex and expensive to make. They also have a certain degree of fragility and require calibration and temperature compensation before they can be used.

Another commonly used pressure gauge is a Bourdon gauge. Such a gauge comprises a fragile, flattened thin-wall, closed-ended tube which is connected at the hollow end to a fixed pipe containing the fluid pressure to be measured. An increase in pressure causes the closed end of the pipe to describe an arc. Such a gauge comprises delicate components which are vulnerable to damage from, for example, exposure to high pressures.

One problem that makes it difficult to accurately measure the amount of gas in a gas vessel is the temperature-pressure relationship of gases contained within the cylinder. According to the gas laws, the pressure exerted by a given quantity of gas at constant volume is directly proportional to its temperature. Therefore, as the temperature of a gas increases, so will the pressure of the gas.

Consequently, the measurement of pressure using a pressure gauge such as a Bourdon gauge goes up and down proportionally to absolute temperature, e.g. from an initial temperature of 20° C. to, for example, 50° C. in an sunlit environment, the indicated pressure on a Bourdon gauge will increase by 10%.

An additional issue is that, in order to determine the contents of a cylinder using a pressure measurement, the pressure gauge is required to be corrected for compressibility of the gas. This is complicated by the behaviour of a gas at high pressure not conforming to the behaviour of an ideal gas.

An alternative type of device used to measure the physical properties of gases is a piezoelectric device such as a quartz crystal. Quartz crystals demonstrate piezoelectric behaviour, i.e. the application of voltage to them results in slight squeezing or stretching of the solid, and vice versa.

"*A Precise And Robust Quartz Sensor Based On Tuning Fork Technology For ($SF_6$)—Gas Density Control*"—Zeisel et al, Sensors and Actuators 80 (2000) 233-236 discloses an arrangement whereby a quartz crystal sensor is used to measure the density of $SF_6$ gas in high and medium voltage electrical equipment at low gas pressures. The measurement of the density of the $SF_6$ gas is critical to the safety of the apparatus. This document describes a low pressure application for quartz sensor technology in which pressures of up to 8 bar g are used.

U.S. Pat. No. 4,644,796 discloses a method and apparatus for measuring the pressure of a fluid using a quartz crystal oscillator housed within a variable-volume housing comprising a bellows arrangement. The internal volume of the housing varies due to compression/expansion of the bellows by external fluid pressure. Consequently, the density of the fluid within the housing varies as the internal volume of the housing varies. The density within the housing can be measured using a quartz crystal oscillator.

The above arrangements describe the use of a solid state sensor such as a quartz crystal oscillator. However, neither of the above arrangements and methods is suitable for accurately measuring the mass of gas in a pressure vessel such as a gas cylinder. Therefore, known measuring arrangements suffer from a technical problem that they are unable to provide accurate measurement of the mass of gas in an enclosure such as a gas cylinder where high pressures are encountered.

According to a first aspect of the present invention, there is provided a method of measuring the mass of a gas under pressure using a piezoelectric oscillator, said gas being contained within a pressure vessel having a fixed internal volume and the piezoelectric oscillator being immersed in the gas within the pressure vessel, the method comprising: a) utilising said piezoelectric oscillator to measure the density of the gas within the high-pressure vessel; b) determining, from the density measurement and from the internal volume of said pressure vessel, the mass of the gas within the pressure vessel.

By providing such a method, the true contents (i.e. mass) of gas (such as a permanent gas) in a pressure vessel such as a cylinder can be measured directly without the need to compensate for factors such as temperature or compressibility. This allows a determination of mass through direct derivation from the density of the gas in the cylinder, reducing the need for additional sensors or complex compensations and approximations to be made. Further, the piezoelectric oscillator is a solid state device which is resistant to high pressures, sudden changes in pressure or other environmental factors. The piezoelectric oscillator is operable to be entirely immersed in the gas, in contrast to conventional gauges (such as a Bourdon gauge) which requires a pressure differential in order to function.

In one embodiment, step a) comprises: driving, by means of a drive circuit, the piezoelectric oscillator such that the piezoelectric oscillator resonates at a resonant frequency; and measuring said resonant frequency over a pre-determined time period to determine the density of gas in said high-pressure vessel.

In one embodiment, steps a) and b) are repeated one or more times such that a series of measurements of the gas density within the pressure vessel over a period of time is obtained, said series of measurements being utilised to determine the change in mass of gas within pressure vessel during said period of time.

In one embodiment, said piezoelectric oscillator comprises a quartz crystal oscillator.

In an embodiment, the quartz crystal comprises at least one tine. In a variation, the quartz crystal comprises a pair of planar tines.

In an embodiment, the quartz crystal is AT cut or SC cut.

In a variation, the surface of the quartz crystal is directly exposed to the gas.

In one embodiment, the sensor assembly comprises a drive circuit. In a variation, the sensor assembly comprises a drive circuit comprising a Darlington pair arranged in a feedback configuration from a common emitter amplifier.

In one embodiment, the sensor assembly comprises a power source. In one arrangement, the power source comprises a lithium-ion battery.

In one embodiment, the sensor assembly comprises a processor.

In one embodiment, the pressure vessel comprises a high pressure vessel. A high pressure vessel is a vessel arranged to withstand internal pressures generally greater than 10 bar.

In a variation, the pressure vessel comprises a gas cylinder.

According to a second aspect of the present invention, there is provided a sensor assembly for measuring the mass of a gas under pressure within a pressure vessel having a fixed internal volume, the sensor assembly comprising a piezoelectric oscillator for immersion in the gas within the pressure vessel, the sensor assembly, when so immersed, being arranged to measure the density of the gas within the pressure vessel and being configured to determine, from the density measurement and from the internal volume of said pressure vessel, the mass of the gas within the pressure vessel.

By providing such an arrangement, the true contents (i.e. mass) of fluid in a pressure vessel such as a cylinder can be measured directly without the need to compensate for factors such as temperature or compressibility. This allows a determination of mass through direct derivation from the density of the gas in the cylinder, reducing the need for additional sensors or complex calculations to be performed. Further, the piezoelectric oscillator is a solid state device which is resistant to high pressures or sudden changes in pressure and, as such, is less likely to become damaged by pressure "creep" or other environmental factors. The structure of the piezoelectric oscillator enables the piezoelectric oscillator to be entirely immersed in the gas, in contrast to conventional gauges (such as a Bourdon gauge) which requires a pressure differential in order to function.

In a variation, said piezoelectric oscillator comprises a quartz crystal oscillator.

In a variation, the gas is a permanent gas.

In one arrangement, the high-pressure vessel is a gas cylinder.

In an embodiment, the sensor assembly comprises a drive circuit. In an embodiment, the sensor assembly comprises a drive circuit comprising a Darlington pair arranged in a feedback configuration from a common emitter amplifier.

In one embodiment, the sensor assembly comprises a power source. In one arrangement, the power source comprises a lithium-ion battery.

In one embodiment, the sensor assembly comprises a processor.

In one embodiment, the sensor assembly is arranged to drive the piezoelectric oscillator such that the piezoelectric oscillator resonates at a resonant frequency and to measure said resonant frequency over a pre-determined time period to determine the density of gas in said pressure vessel.

In one embodiment, the sensor assembly is further arranged to perform repeat measurements of the mass of the gas within the pressure vessel at discrete time intervals to obtain a plurality of measurements, and to determine, from said plurality of measurements, the mass flow of gas to/from the pressure vessel during the discrete time intervals. more times such that a series of measurements of the gas density within the pressure vessel over a period of time is obtained, said series of measurements being utilised to determine the change in mass of gas within pressure vessel during said period of time.

According to a third aspect of the present invention, there is provided a valve arrangement comprising the sensor assembly of the second aspect, the valve arrangement being for connection to a pressure vessel body to form the pressure vessel having a fixed internal volume, the valve arrangement being arranged to enable selective filling of the pressure vessel with gas or dispensation of gas from the pressure vessel.

According to a fourth aspect of the present invention, there is provided a pressure vessel for containing a gas under pressure, the pressure vessel having a fixed internal volume and comprising: a pressure vessel body defining a fixed internal volume; a valve arrangement connected to said vessel body and arranged to enable selective filling of the pressure vessel with gas or dispensation of gas from said vessel; and the sensor assembly of the second aspect.

In one embodiment, the sensor assembly comprises a drive circuit. In one embodiment, the sensor assembly comprises a power source. In a variation, the power source comprises a lithium-ion battery.

In one embodiment, the sensor assembly is located entirely within the fixed internal volume of the pressure vessel.

In one arrangement, the pressure vessel body comprises a gas cylinder.

According to a fifth embodiment of the present invention, there is provided a computer program product executable by a programmable processing apparatus, comprising one or more software portions for performing the steps of the first aspect.

According to a sixth embodiment of the present invention, there is provided a computer usable storage medium having a computer program product according to the fourth aspect stored thereon.

Embodiments of the present invention will now be described in detail with reference to the accompanying drawings, in which:

FIG. 1 shows a schematic view of a gas cylinder assembly 10 according to an embodiment of the invention.

Figure 1:
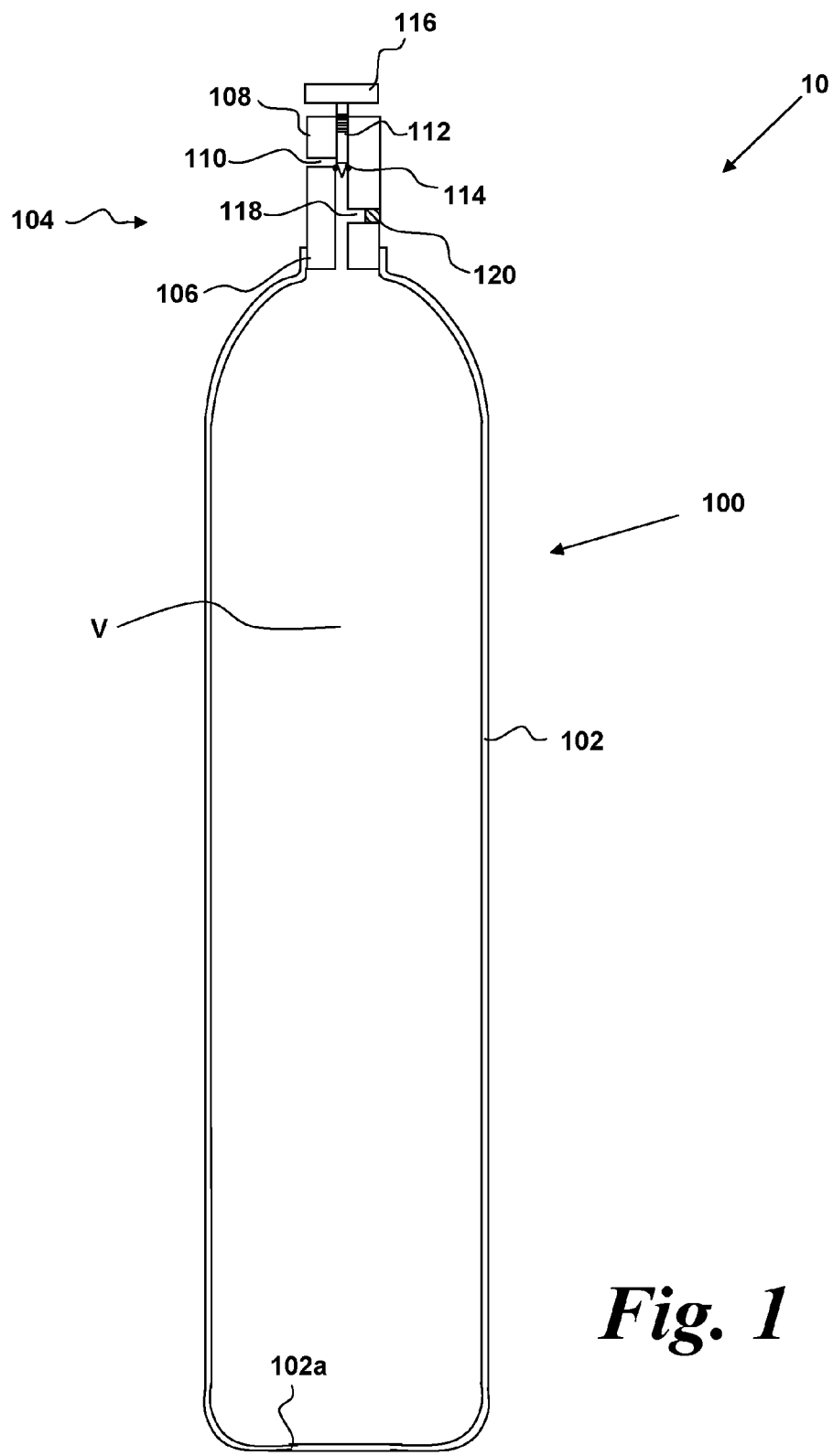
FIG. 1 is a schematic diagram of a gas cylinder assembly.

The gas cylinder assembly 10 comprises a gas cylinder 100 having a gas cylinder body 102 and a valve 104. The gas cylinder body 102 comprises a generally cylindrical container having a flat base 102a arranged to enable the gas cylinder 100 to stand unsupported on a flat surface.

The gas cylinder body 102 is formed from steel, aluminium and/or composite materials and is adapted and arranged to withstand internal pressures up to approximately 900 bar g. An aperture 106 is located at a proximal end of the gas cylinder body 102 opposite to the base 102a and comprises a screw thread (not shown) adapted to receive the valve 104.

The gas cylinder body 102 and valve 104 define a pressure vessel (in this embodiment, in the form of the gas cylinder 100) having an internal volume V. The internal volume V is fixed. By this is meant that the structure of the gas cylinder 100 is such that the internal volume V thereof (and, concomitantly, the volume of a gas contained therein) can be assumed not to vary by a significant degree in use, storage or in dependence upon environmental conditions such as temperature, pressure or humidity. The internal volume V of the gas cylinder 100 is intended to include the entire volume within the gas cylinder body 102 and the valve 104. In other words, the internal volume V is the total internal volume within the gas cylinder assembly 10 where gas is held under pressure.

Any suitable fluid may be contained within the gas cylinder assembly 100. However, the present embodiment relates to, but is not exclusively limited to, purified permanent gases which are free from impurities such as dust and/or moisture. Non-exhaustive examples of such gases may be: Oxygen, Nitrogen, Argon, Helium, Hydrogen, Methane, Nitrogen Trifluoride, Carbon Monoxide, Krypton or Neon.

The valve 104 comprises a housing 108, an outlet 110, a valve body 112 and a valve seat 114. The housing 108 comprises a complementary screw thread for engagement with the aperture 106 of the gas cylinder body 102. The outlet 110 is adapted and arranged to enable the gas cylinder 100 to be connected to other components in a gas assembly; for example, hoses, pipes, or further pressure valves or regulators. The valve 104 may, optionally, comprise a VIPR (Valve with Integrated Pressure Regulator).

The valve body 112 can be axially adjusted towards or away from the valve seat 114 by means of rotation of a graspable handle 116 selectively to open or to close the outlet 110. In other words, movement of the valve body 112 towards or away from the valve seat 112 selectively controls the area of the communication passageway between the interior of the gas cylinder body 102 and the outlet 110. This, in turn, controls the flow of gas from the interior of the gas cylinder assembly 100 to the external environment.

A through-hole 118 is formed in the housing 108 downstream of the outlet 110. The through-hole 118 is closed by means of a feed through 120 which enables components (such as wires) to be fed through from external of the gas cylinder 100 to the interior of the gas cylinder 100. The feed through 120 functions as a high pressure seal maintaining the integrity of the gas cylinder 100.

The gas cylinder assembly 10 is provided with a sensor assembly 200. The sensor assembly 200 is arranged to measure the density of the gas within the internal volume V of the gas cylinder 100. The sensor assembly 200 is shown in greater detail in FIGS. 2 and 3 and comprises a quartz crystal oscillator 202 connected to a drive circuit 204 and a battery 206 by suitable wiring 208. A processor 220 (not shown in FIGS. 2 and 3) may also be provided, either separately or as part of the drive circuit 204. This will be described later.

Figure 2:
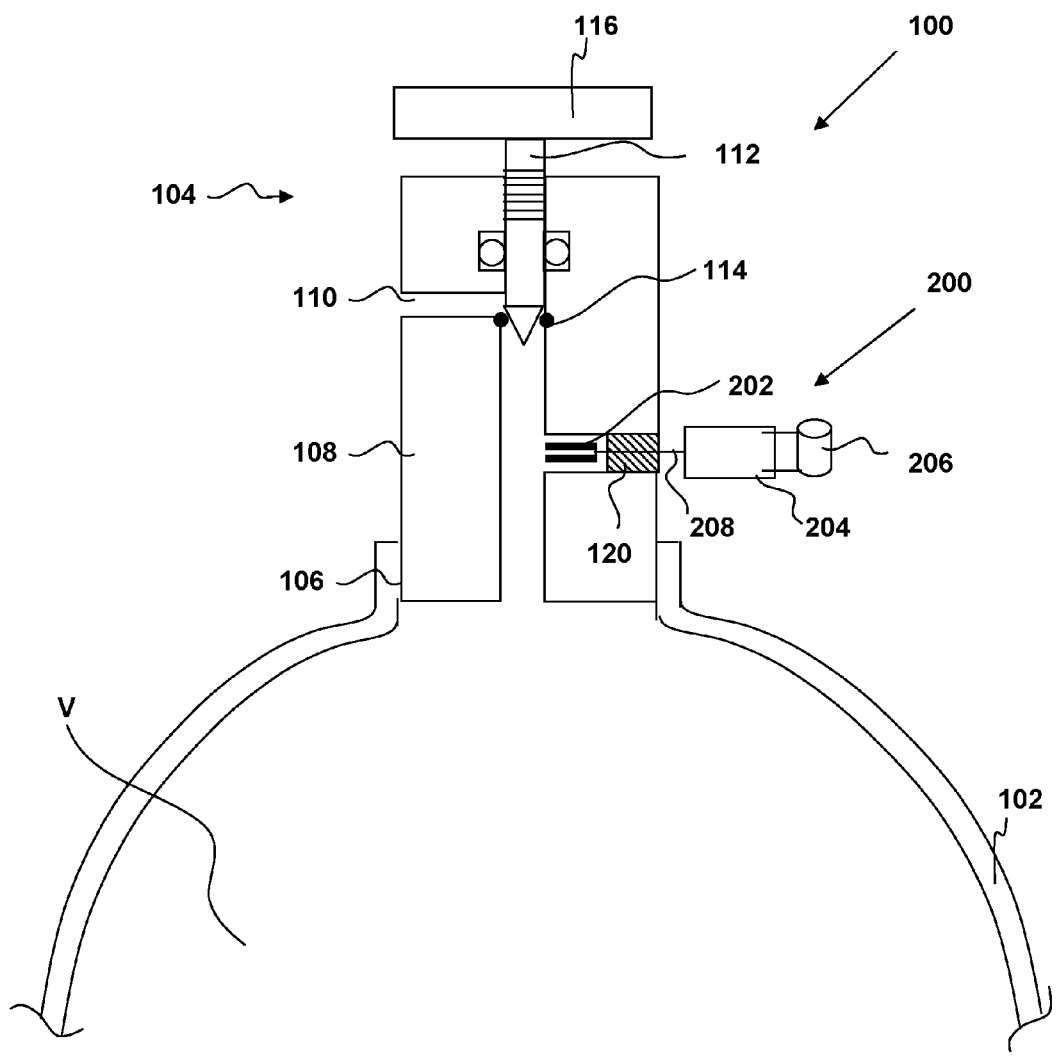
FIG. 2 is a schematic diagram showing an upper part of the gas cylinder assembly according to a first embodiment of the invention.

In the embodiment shown in FIG. 2, the quartz crystal oscillator 202 is located within the internal volume V of the gas cylinder 100 and the drive circuit 204 is located outside the gas cylinder 100. Consequently, at least a part of the sensor assembly 200 is located in the through-hole 118. The quartz crystal oscillator 202 and the drive circuit 204 are connected by the wiring 208 which passes through the high pressure feed through 120.

In this arrangement, the quartz crystal oscillator 202 is constantly under isostatic pressure within the internal volume V of the gas cylinder 100 and, consequently, does not experience a pressure gradient. In other words, any mechanical stress originating from the pressure difference between the internal volume V of the gas cylinder 100 and the external environment is across the feed through 120.

Figure 3:
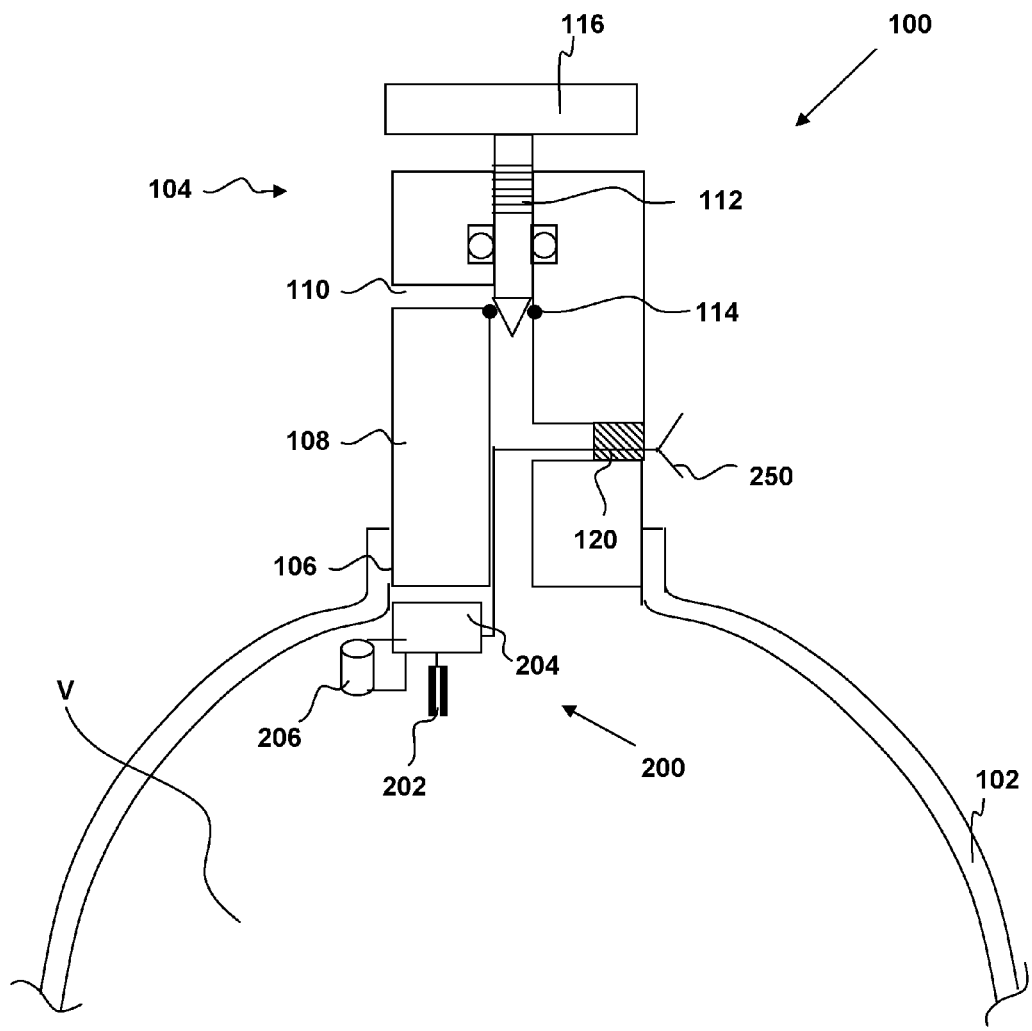
FIG. 3 is a schematic diagram showing an upper part of the gas cylinder assembly according to a second embodiment of the invention.

An alternative embodiment is shown in FIG. 3. The features of the embodiment shown in FIG. 3 which are in common with the embodiment of FIG. 2 are allocated the same reference numerals and will not be described again here.

In the embodiment of FIG. 3, the whole of the sensor assembly 200 is located within the internal volume V of the gas cylinder 100. Therefore, the quartz crystal oscillator 202, the drive circuit 204 (and processor 220, if provided) and the battery 206 are all located within the internal volume V of the gas cylinder 100. The components of the sensor assembly 200 are completely immersed in the gas and are under isostatic gas pressure within the gas cylinder 100. Consequently, the sensor assembly 200 experiences the full gas pressure of the gas within the gas cylinder 100.

In this embodiment, the feed through 120 may optionally be deleted. Alternatively, the sensor assembly 200 may be connected to an antenna 250 for remote communication with, for example, a base station. This will be discussed later. In this case, the antenna 250 may be located outside the gas cylinder 100 and connected to the sensor assembly by means of a wire or equivalent connector. The wire could be passed through the feed through 120 in order to effect a connection between the antenna 250 and the sensor assembly 200.

The antenna 250 itself may be adapted and arranged to use any suitable communication protocol; for example, a non-exhaustive list may be RFID, Bluetooth, Infra red (IR), 802.11 wireless, frequency modulation (FM) transmission or a cell network.

Alternatively, one-wire communication may be implemented. One-wire communication needs only a single metallic conductor to communicate: the 'return' path of the circuit is provided by capacitive coupling through the air between the communicating devices. The skilled person would be readily aware of alternatives of the antenna 250 (and associated transmission hardware) which could be used with the embodiments discussed herein.

The inventors have found that only a few components of the sensor assembly 200 are sensitive to high pressure. In particular, larger components such as batteries can be susceptible to high pressures. However, it has been found that lithium ion batteries perform particularly well under the high pressures encountered within the gas cylinder 100. Consequently, the battery 206 comprises lithium ion cells. However, alternative suitable power sources would be readily be contemplated by the skilled person.

The location of the complete sensor assembly 200 entirely within the gas cylinder 100 provides additional flexibility when configuring gas cylinders 100. In particular, location of relatively fragile electronic components entirely within the strong metal or composite walls of the gas cylinder 100 provides considerable protection from environmental or accidental damage. This is particularly important, for example, in storage areas or depots, where gas cylinders 100 are located adjacent other gas cylinders 100, heavy machinery or rough surfaces.

Further, the location of the electronic components of the sensor assembly entirely within the internal volume V of the gas cylinder 100 enables larger components to be provided which otherwise might not be suitable for use on the external surface of a cylinder 100. For example, a larger battery may be provided in order to increase the operational lifetime of the sensor assembly 200.

Additionally, the internal location of the sensor assembly 200 protects the electronic components from environmental conditions such as salt, water and other contaminants. This would allow, for example, a high impedance circuit which is highly sensitive to salt and water damage to be used as part of the sensor assembly 200.

However, in a variation of the above embodiments, part of the sensor assembly may be located within the internal volume V of the gas cylinder 100 and a part may be located externally thereof. For example, the drive circuit 212 and processor 220 may be located within the gas cylinder 100 whilst the battery 206 may be located outside the gas cylinder 100. This arrangement enables the more fragile components of the sensor assembly to be protected from damage and contaminants, whilst the battery 206 is readily accessible for maintenance and replacement.

With regard to external communication, in one configuration, an external aerial or antenna (such as antenna 250) is not explicitly required. For example, communication may be effected by means of acoustic transmission from within the cylinder 100. Acoustic transmission may be effected by a transmitter located within the gas cylinder 100. The transmitter may comprise, for example, a simple fixed-frequency piezoelectric resonator.

A complementary receiver is also required and this component may be located remote from the cylinder 100 and may comprise hardware such as, for example, a phase-locked loop tone detector integrated with a microphone. Such an acoustic arrangement provides the advantage that no feed-through is required (as is the case for the antenna 250) and that all of the electronic components can be located entirely within the cylinder 100.

The benefits of internal location of the sensor assembly 200 are unique to solid state sensor devices such as the quartz crystal oscillator 202. For example, a conventional pressure sensor such as a Bourdon gauge cannot be located in this manner. Whilst a crystal-based sensor can operate totally immersed in gas at constant pressure, a conventional pressure sensor is unable to measure isostatic pressure and requires a pressure gradient in order to function. Consequently, a conventional pressure gauge must be located between the high pressure to be measured and the atmosphere. This precludes the location of a conventional pressure gauge entirely within a gas cylinder 100.

The sensor assembly 200 will now be described in more detail with reference to FIGS. 2 to 4. The quartz crystal oscillator 202 comprises a small, thin section of cut quartz. Quartz demonstrates piezoelectric behaviour, i.e. the application of a voltage across the crystal causes the crystal to change shape, generating a mechanical force. Conversely, a mechanical force applied to the crystal produces an electrical charge.

Two parallel surfaces of the quartz crystal oscillator 202 are metallised in order to provide electrical connections across the bulk crystal. When a voltage is applied across the crystal by means of the metal contacts, the crystal changes shape. By application of an alternating voltage to the crystal, the crystal can be caused to oscillate.

The physical size and thickness of the quartz crystal determines the characteristic or resonant frequency of the quartz crystal. Indeed, the characteristic or resonant frequency of the crystal 202 is inversely proportional to the physical thickness between the two metallised surfaces. Quartz crystal oscillators are well known in the art and so the structure of the quartz crystal oscillator 202 will not be described further here.

The resonant vibration frequency of a quartz crystal will vary depending upon the environment in which the crystal is located. In a vacuum, the crystal will have a particular frequency. However, this frequency will change in different environments. For example, in a fluid, the vibration of the crystal will be damped by the surrounding molecules of the fluid and this will affect the resonant frequency and the energy required to oscillate the crystal at a given amplitude.

Further, adsorption of gas or deposition of surrounding materials onto the crystal will affect the mass of the vibrating crystal, altering the resonant frequency. This forms the basis for commonly used selective gas analysers in which an absorbing layer is formed on the crystal and increases in mass as gas is absorbed onto the absorbing layer. However, in the present case, no coating is applied to the quartz crystal oscillator 202. Indeed, adsorption or deposition of material onto the quartz crystal oscillator 202 is undesirable in the present case since the accuracy of the measurement may be affected.

The quartz crystal oscillator 202 of the present embodiment is tuning fork-shaped and comprises a pair of tines 202a (FIG. 4) approximately 5 mm long arranged to oscillate at a resonant frequency of 32.768 kHz. The tines 202a of the fork oscillate normally in their fundamental mode, in which they move synchronously towards and away from each other at the resonant frequency.

Additionally, it is desirable to use quartz which is AT cut or SC cut. In other words, a planar section of quartz is cut at particular selected angles so that the temperature coefficient of the oscillation frequency can be arranged to be parabolic with a wide peak around room temperature. Therefore, the crystal oscillator can be arranged such that the slope at top of the peak is precisely zero.

Such crystals are commonly available at relative low cost. In contrast to the majority of quartz crystal oscillators which are used in vacuo, in the present embodiment the quartz crystal oscillator 202 is exposed to the gas under pressure in the internal volume V of the gas cylinder 100.

Figures 4, 5:
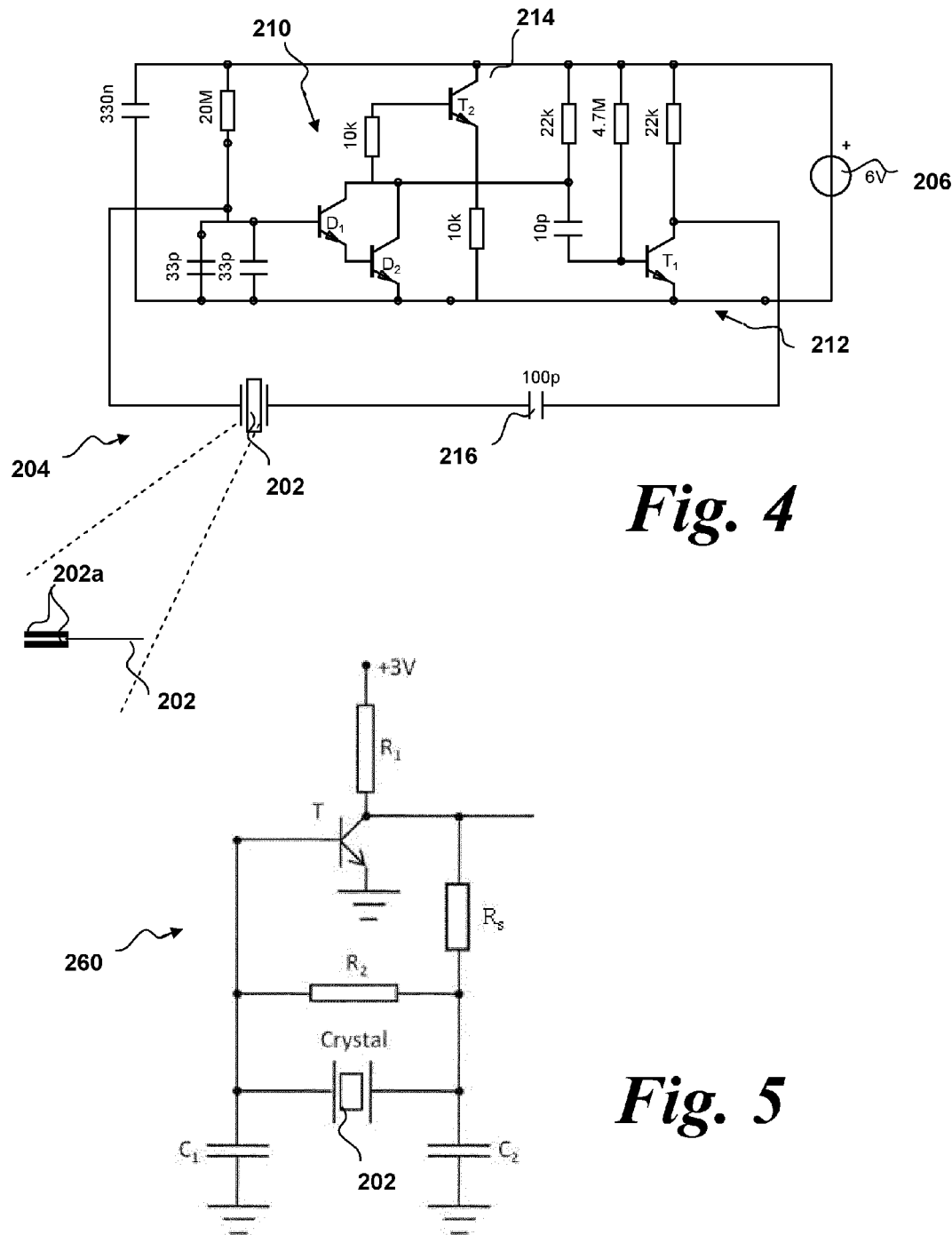
FIG. 4 is a schematic diagram of a drive circuit for use with the first or second embodiments.
FIG. 5 is a schematic diagram showing an alternative the drive circuit for use with the first or second embodiments.

The drive circuit 204 for driving the quartz crystal oscillator 202 is shown in FIG. 4. The drive circuit 204 must meet a number of specific criteria. Firstly, the quartz crystal oscillator 202 of the present invention may be exposed to a range of gas pressures; potentially, the pressures may vary from atmospheric pressure (when the gas cylinder 100 is empty) to around 900 bar g if the gas cylinder contains a pressurised gas such as hydrogen. Thus, the quartz crystal 202 is required to operate (and restart after a period of non-use) under a wide range of pressures.

Consequently, the quality (Q) factor of the quartz crystal oscillator 202 will vary considerably during use. The Q factor is a dimensionless parameter relating to the rate of damping of an oscillator or resonator. Equivalently, it may characterise the bandwidth of a resonator relative to its centre frequency.

In general, the higher the Q factor of an oscillator, the lower the rate of energy loss relative to the stored energy of the oscillator. In other words, the oscillations of a high Q factor oscillator reduce in amplitude more slowly in the absence of an external force. Sinusoidally driven resonators having higher Q factors resonate with greater amplitudes at the resonant frequency but have a smaller bandwidth of frequencies around that frequency for which they resonate.

The drive circuit 204 must be able to drive the quartz crystal oscillator 202 despite the changing Q factor. As the pressure in the gas cylinder 100 increases, the oscillation of the quartz crystal oscillator 202 will become increasingly damped, and the Q factor will fall. The falling Q factor requires a higher gain to be provided by an amplifier in the drive circuit 204. However, if too high an amplification is provided, the drive circuit 204, the response from the quartz crystal oscillator 202 may become difficult to distinguish. In this case, the drive circuit 204 may simply oscillate at an unrelated frequency, or at the frequency of a non-fundamental mode of the quartz crystal oscillator 202.

As a further limitation, the drive circuit 204 must be low power in order to run on small low power batteries for a long time with or without supplementary power such as photovoltaic cells.

The drive circuit 204 will now be described with reference to FIG. 4. In order to drive the quartz crystal oscillator 202, the drive circuit 204 essentially takes a voltage signal from the quartz crystal oscillator 202, amplifies it, and feeds that signal back to the quartz crystal oscillator 202. The fundamental resonant frequency of the quartz crystal oscillator 202 is, in essence, a function of the rate of expansion and contraction of the quartz. This is determined in general by the cut and size of the crystal.

However, external factors also affect the resonant frequency. When the energy of the generated output frequencies matches the losses in the circuit, an oscillation can be sustained. The drive circuit 204 is arranged to detect and maintain this oscillation frequency. The frequency can then be measured by the processor 220, used to calculate the appropriate property of the gas required by the user and, if required, output to a suitable display means (as will be described later).

The drive circuit 204 is powered by a 6 V power source 206. The power source 206, in this embodiment, comprises a lithium ion battery. However, alternative power sources will be readily apparent to the person skilled in the art; for example, other battery types both rechargeable and non-rechargeable and a solar cell arrangement.

The drive circuit 204 further comprises a Darlington pair Common Emitter amplifier 210. A Darlington pair comprises a compound structure consisting of two bipolar NPN transistors configured such that the current amplified by a first of the transistor is amplified further by the second one. This configuration enables a higher current gain to be obtained when compared to each transistor being taken separately. Alternative, PNP bipolar transistors may be used.

The Darlington pair 210 is arranged in a feedback configuration from a single transistor ($T_1$) Common Emitter amplifier 212. A NPN bipolar junction transistor is shown in FIG. 4. However, the skilled person would be aware of alternative transistor arrangements which may be used; for example, a bipolar junction PNP transistor or Metal Oxide Semiconductor Field Effect Transistors (MOSFETs).

The drive circuit 204 comprises a further NPN emitter follower transistor $T_2$ which acts as a buffer amplifier 214. The buffer amplifier 214 is arranged to function as a buffer between the circuit and the external environment.

A capacitor 216 is located in series with the quartz crystal oscillator 202. The capacitor 216, in this example, has a value of 100 pF and enables the drive circuit 204 to drive the quartz crystal oscillator 202 in situations where the crystal has become contaminated, for example by salts or other deposited materials.

An alternative drive circuit 260 will now be described with reference to FIG. 5. The drive circuit shown in FIG. 5 is configured similarly to a Pierce oscillator. Piece oscillators are known from digital IC clock oscillators. In essence, the drive circuit 260 comprises a single digital inverter (in the form of a transistor) T, three resistors $R_1$, $R_2$ and $R_S$, two capacitors $C_1$, $C_2$, and the quartz crystal oscillator 202.

In this arrangement, the quartz crystal oscillator 202 functions as a highly selective filter element. Resistor $R_1$ acts as a load resistor for the transistor T. Resistor $R_2$ acts as a feedback resistor, biasing the inverter T in its linear region of operation. This effectively enables the inverter T to operate as a high gain inverting amplifier. Another resistor $R_S$ is used between the output of the inverter T and the quartz crystal oscillator 202 to limit the gain and to dampen undesired oscillations in the circuit.

The quartz crystal resonator 202, in combination with $C_1$ and $C_2$ forms a Pi network band-pass filter. This enables a 180 degree phase shift and a voltage gain from the output to input at approximately the resonant frequency of the quartz crystal oscillator. The above described drive circuit 260 is reliable and cheap to manufacture since it comprises relatively few components.

As discussed above, the sensor assembly 200 may include a processor 220 which receives inputs from the quartz crystal oscillator 202 and drive circuit 204. The processor 220 may comprise and suitable arrangement, such as an Application Specific Integrated Circuit (ASIC) or Field Programmable Gate Array (FPGA). The processor 220 is programmed to calculate, display and communicate parameters useful to users of the cylinder 100.

When used with the quartz crystal oscillator 202, the processor 220 may be configured to measure the frequency f or period of the signal from the drive circuit 204. This may be achieved by, for example, counting oscillations over a fixed time, and convert that frequency into a density value using an algorithm or look-up table. This value is passed to the processor 220 which is configured to perform, based on the supplied inputs, a calculation to determine the mass of the gas in the gas cylinder 100.

The processor 220 may, optionally, be designed for mass production to be identical in all cylinders, with different features in the software and hardware enabled for different gases.

Additionally, the processor 220 may also be configured to minimise power consumption through implementation of standby or "sleep" modes which may cover the processor 220 and additional components such as the drive circuit 204 and quartz crystal oscillator 202.

Various schemes may be implemented; for example, the processor 220 may be on standby for 10 seconds out of every 11 seconds. Further, the processor 220 may control the quartz crystal oscillator 202 and drive circuit 204 such that these components are put on standby for the majority of time, only being switching the more power hungry components on for ½ second every 30 seconds. Alternatively or additionally, communication components such as the antenna 250 can be switched off as required or used to activate the sensor assembly 200.

The theory and operation of the sensor assembly 200 will now be described with reference to FIGS. 6 to 9.

The quartz crystal oscillator 202 has a resonant frequency which is dependent upon the density of the fluid in which it is located. Exposing an oscillating tuning fork-type crystal oscillator to a gas leads to a shift and damping of the resonant frequency of the crystal (when compared to the resonant frequency of the crystal in a vacuum). There are a number of reasons for this. Whilst there is a damping effect of the gas on the oscillations of the crystal, the gas adheres to the vibrating tines of the tuning fork crystal oscillator 202 which increases the mass of the oscillator. This leads to a reduction in the resonant frequency of the quartz crystal oscillator according to the motion of a one-sided, fixed elastic beam:

$$\frac{\Delta \omega}{\omega_0} = \frac{\rho t}{2\rho_q w}\left(c_1 + c_2 \frac{\partial}{t}\right) \quad 1)$$

Where $$\frac{\Delta \omega}{\omega_0}$$

is the relative change in resonant angular frequency, $\rho$ is the gas density, t is the thickness of the quartz oscillator, $\rho_q$ is the density of the quartz oscillator and w is the width of the fork. $c_1$ and $c_2$ are geometrically dependent constants and $\partial$ is the thickness of the surface layer of gas as defined by:

$$\partial = \sqrt{\frac{2\eta}{\rho \omega_0}} \quad 2)$$

Where $\eta$ is the temperature dependent viscosity of the gas.

The two parts of equation 1) relate to a) the additive mass of the gas on the tines of the quartz crystal oscillator 202 and to b) the shear forces arising on the outermost surface layer of the tines during oscillation.

The equation can thus be rewritten in terms of frequency and simplified to:

$$\Delta f = A\rho + B\sqrt{\rho} + C \quad 3)$$

Where $$A = \frac{c_1 t}{2\rho_q w} f_0, \; B = \frac{c_2}{2\rho_q w}\sqrt{\frac{\eta}{\pi}}\sqrt{f_0}$$

and C is an offset constant and $f_0$ is the natural resonant frequency of the crystal in a vacuum.

It has been found by the inventors that a suitably good approximation can be obtained by approximating:

$$\Delta f \approx A\rho \quad 4)$$

Figure 6:
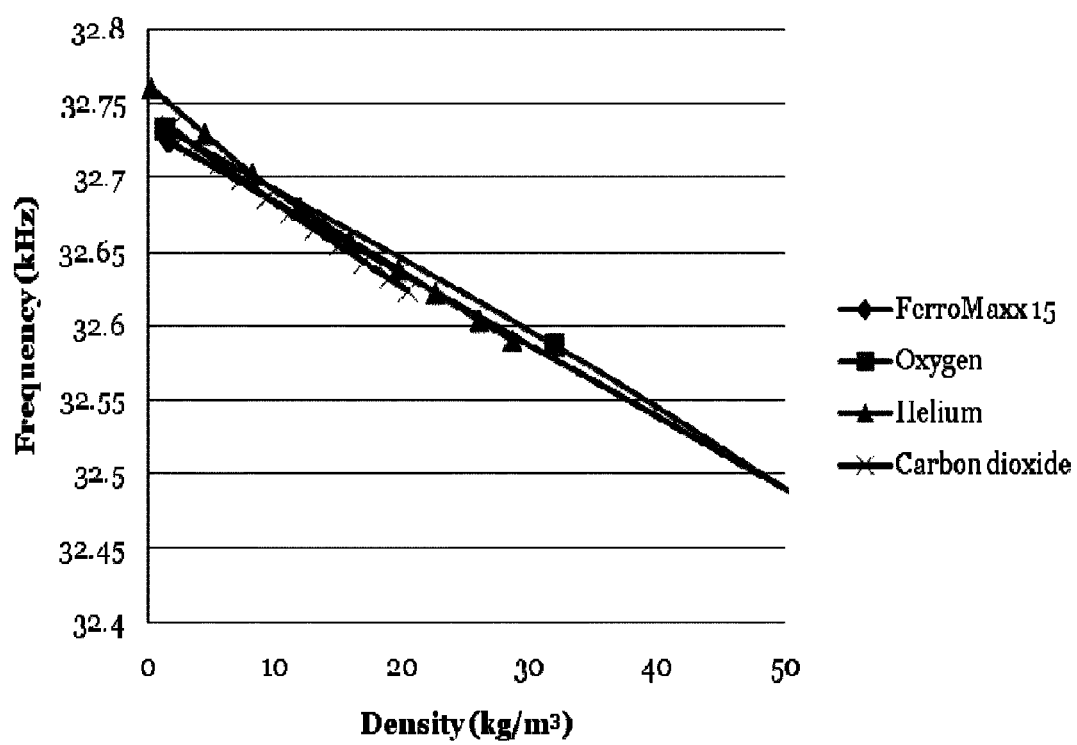
FIG. 6 shows a graph of quartz crystal frequency (kHz) on the Y-axis as a function of density ($kg/m^3$) for a number of different gases.

Consequently, to a good approximation, the change in frequency is proportional to the change in density of the gas to which the quartz crystal oscillator is exposed. FIG. 6 shows, for a number of different gases/gas mixtures, that the resonant frequency of the quartz crystal oscillator 202 varies linearly as a function of density.

In general, the sensitivity of the quartz crystal oscillator 202 is that a 5% change in frequency is seen with, for example, Oxygen gas (having Atomic mass number 32) at 250 bar when compared to atmospheric pressure. Such pressures and gas densities is typical of the storage cylinders used for permanent gases, which are normally between 137 and 450 bar g for most gases, and up to 700 or 900 bar g for helium and hydrogen.

The quartz crystal oscillator 202 is particularly suitable for use as a density sensor for commercially-supplied gases. Firstly, in order to sense accurately the density of a gas, it is necessary for the gas to be free from dust and droplets of liquids, which is guaranteed with commercially supplied gases, but not with air or in the generality of pressure monitoring situations.

Secondly, because the gas pressure within a cylinder can only change slowly during normal use (i.e. as gas is exhausted through the outlet 110), the fact that the quartz crystal oscillator 202 takes a small amount of time (approximately 1 second) to take a reading does not impact the accuracy of measurement. The time period of approximately 1 is required because of the need to count oscillations and because of the need for the quartz crystal oscillator 202 to reach equilibrium at a new gas pressure.

This method may be less accurate if the gas in the gas cylinder 100 is not uniform—for example, if the gas is a non-uniform mixture such as may occur within a partially liquid-filled cylinder or in the case of a recently prepared and insufficiently mixed mixture of light and heavy gases. However, this is unlikely to occur in most packaged gas applications.

As previously described, the internal volume V of gas within the gas cylinder 100 is fixed. Therefore, once the density $\rho$ of the gas within the internal volume V of the gas cylinder 100 has been obtained from measurement by the sensor assembly 200, the mass M of the gas in the cylinder can be obtained from the following equation:

$$M = \rho V \quad 5)$$

The direct measurement of the density ρ of the gas, therefore, enables the calculation of the mass of gas remaining in the gas cylinder 100.

Measurement of the mass of gas in this way has a number of advantages over known arrangements. For example, the mass measured according to an embodiment of the invention is corrected intrinsically for temperature. In contrast, the measurement of pressure using, for example, a Bourdon gauge varies proportionally with absolute temperature. Therefore, the present arrangement does not require temperature measurement and/or correction as is the case with known arrangements.

Further, the mass of gas measured according to an embodiment of the present invention is intrinsically corrected for compressibility Z. In a conventional arrangement, for example, utilising a Bourdon gauge in order to obtain gas contents from pressure, the compressibility of the gas needs to be corrected for. This is particularly important at high pressures, where the compressibility Z is not proportional to the gas pressure in the way expected of an ideal gas.

Figure 7:
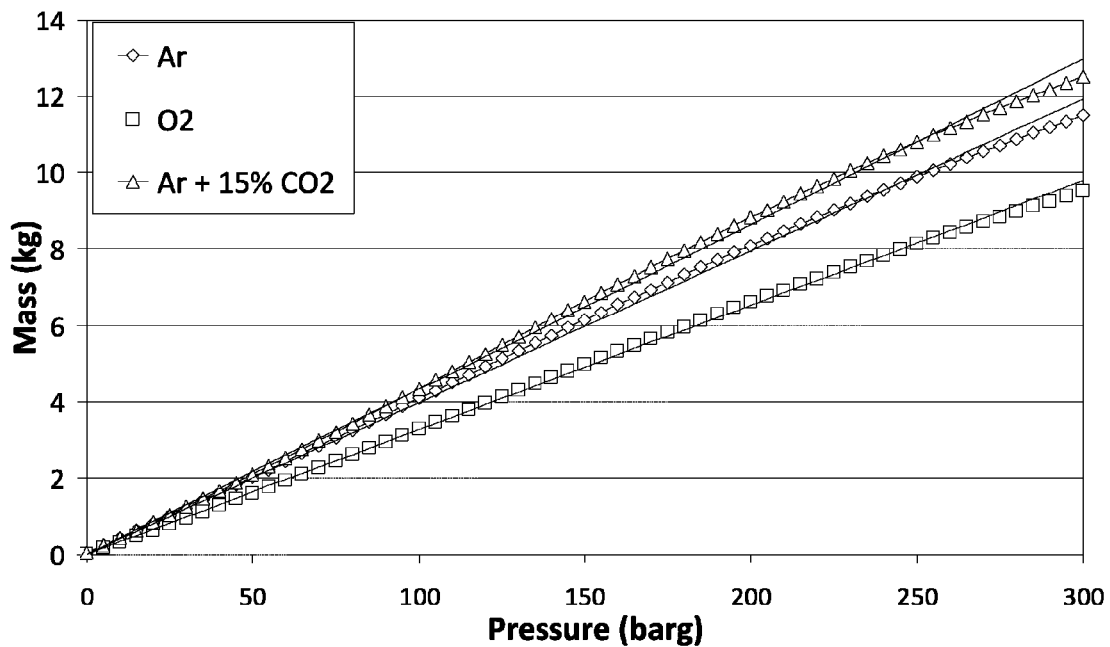
FIG. 7 shows a graph of gas mass (in kg) on the Y-axis as a function of pressure (bar g) on the X-axis for Argon, Oxygen and an Argon: Carbon Dioxide mixture.

The automatic compensation for compressibility is illustrated with reference to FIGS. 7 and 8. FIG. 7 shows a graph of gas mass (in kg) on the Y-axis as a function of Pressure (bar g) for Argon, Oxygen and an Argon: Carbon Dioxide mixture. As shown in FIG. 7, the masses of the different gases vary with increasing pressure. Further, at high pressures in excess of 250 bar g, there is no longer a linear relationship between mass and pressure.

Figure 8:
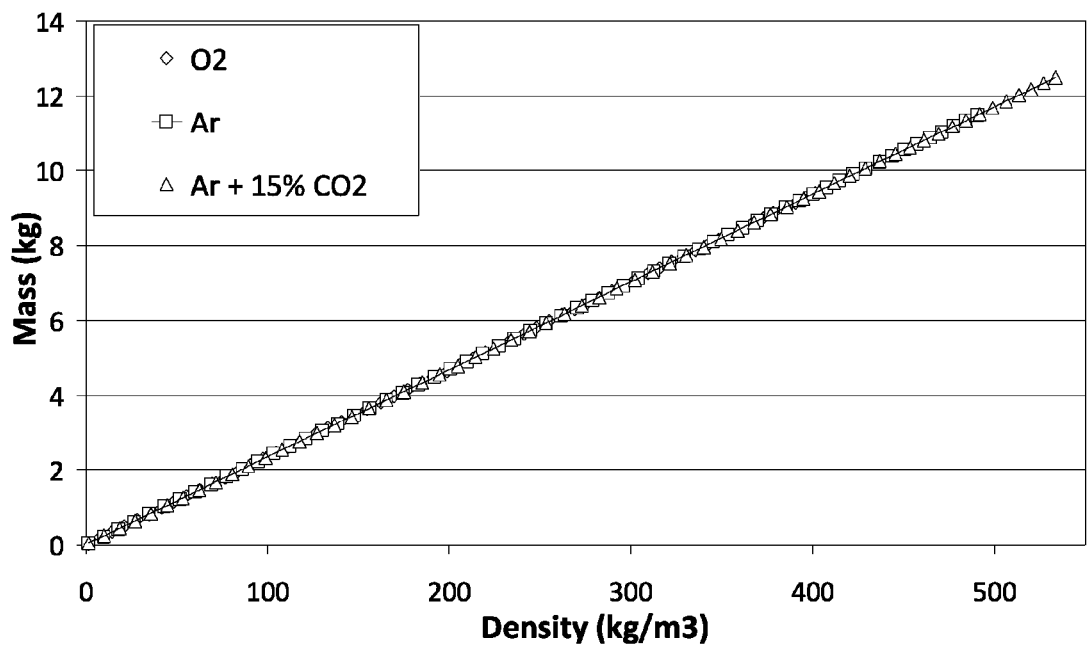
FIG. 8 shows a graph of gas mass (in kg) on the Y-axis as a function of density (in $kg/m^3$) on the X-axis for the same three gases (Argon, Oxygen and an Argon: Carbon Dioxide mixture) as shown in FIG. 7.

FIG. 8 shows a graph of gas mass (in kg) on the Y-axis as a function of Density (in kg/m³) for the same three gases (Argon, Oxygen and an Argon: Carbon Dioxide mixture) as FIG. 7. In contrast to FIG. 7, it can be seen that the mass of gas as a function of density is identical for each gas/gas mixture. Further, the relationship is still linear at high densities. Consequently, the quartz crystal oscillator 202 can be both high resolution and highly linear with density.

As outlined above, the arrangement of the present invention enables mass measurement to very high accuracy with a resolution of parts per million. Coupled with the linear response of the quartz density sensor 202 at high densities and pressures (as illustrated in FIGS. 7 and 8), the high accuracy enables very light gases such as $H_2$ and He to be measured accurately.

In addition to measurement of the static pressure within a gas cylinder 100, the sensor assembly 200 is capable of measuring mass flow into or from the gas cylinder 100. This may be useful in situations where the usage rate of gas from the gas cylinder 100 is required, perhaps to calculate the time remaining before the cylinder is emptied. Alternatively or additionally, the mass flow can be monitored in order to administer precise quantities of gas.

Gas density at atmospheric pressure is only on the order of 1 g/liter, and normal gas usage rates are often just a few liters per minute. The inventors have found that the quartz crystal oscillator 202 is sufficiently stable and accurate to enable mass flow of gas exiting the gas cylinder 100 in to be measured by means of the changing density indicated. The mass flow $$\frac{\partial M}{\partial t}$$

is calculated from equation 6):

$$\frac{\partial M}{\partial t} = V \frac{\Delta \rho}{\Delta t} \quad 6)$$

where V is the volume, Δρ the change in density indicated over time interval Δt. In this instance, the operation of the sensor assembly 200 requires the drive circuit 204 to integrate over a number of oscillation cycles of the quartz crystal oscillator 202. Therefore, it is not possible to obtain an instantaneous rate of change of density with time, $$\frac{\partial \rho}{\partial t}.$$

However, the rate of change of density with time is relatively low in a gas cylinder 100 under normal operation. Therefore, the measurement taken using the sensor assembly 200 is sufficiently accurate in normal use.

Figure 9:
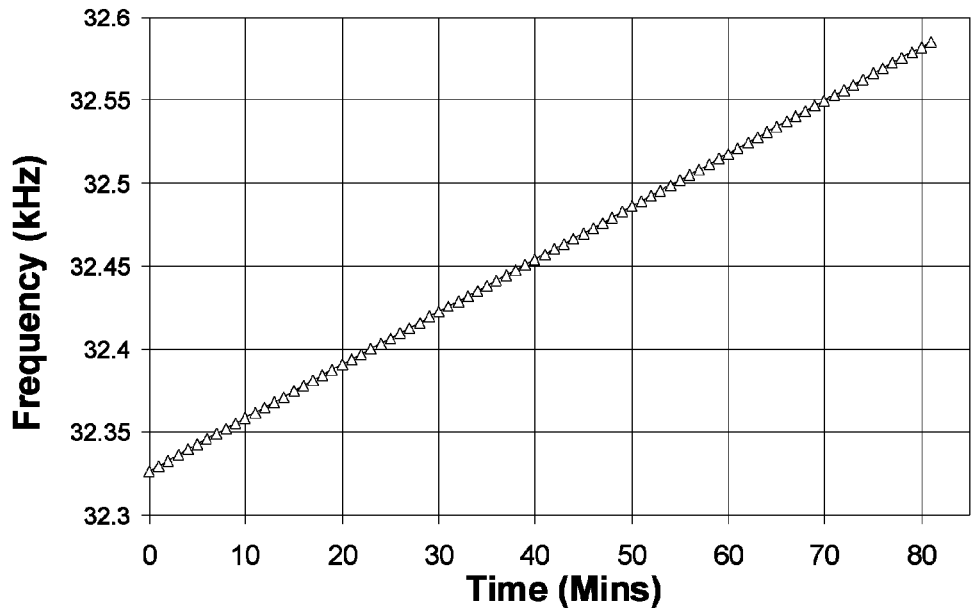
FIG. 9 shows a graph of frequency (in kHz) on the Y-axis as a function of time (in minutes) on the X-axis for a flow rate of 121/min from a 50 liter gas cylinder at a pressure of 100 bar g.
Figure 10:
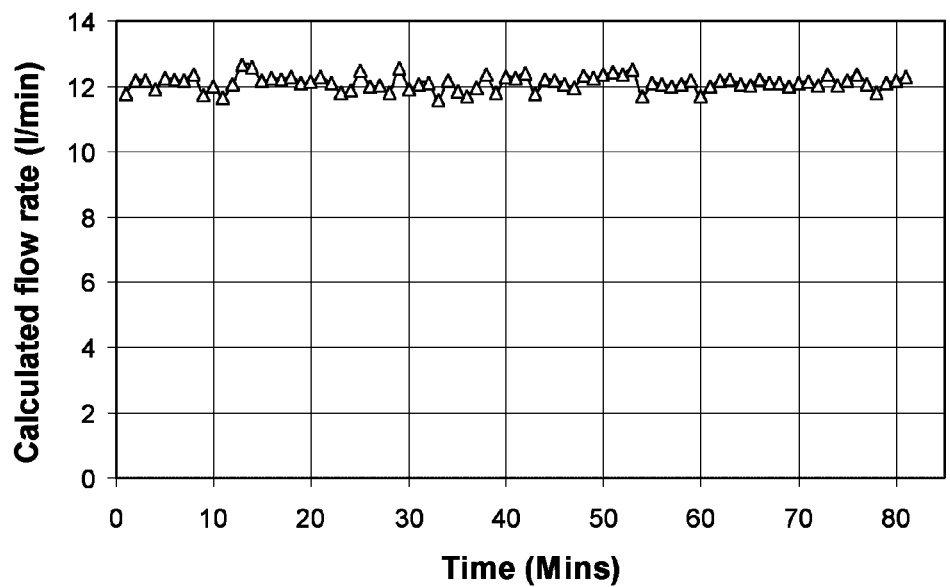
FIG. 10 shows a graph of the calculated flow rate (in liters per minute) on the Y-axis as a function of time (in minutes) on the X-axis for the 50 liter cylinder at a pressure of 100 bar g.

FIGS. 9 and 10 illustrate experimental data of mass flow detection. FIG. 9 shows a graph of frequency (kHz) on the Y-axis as a function of time (in minutes) on the X-axis for a 12 liter per minute flow rate from a 50 liter cylinder at ~100 bar pressure indicated. FIG. 10 shows a graph of the calculated flow rate (in liters per minute) on the Y-axis as a function of time (in minutes) on the X-axis for the 50 liter cylinder at ~100 bar pressure.

These figures illustrate that, for most normal uses, the mass flow rate of gas from a gas cylinder 100 can be determined from a measurement of change of density with time. Consequently, the mass flow rate can be calculated with sufficient accuracy and time resolution using the quartz crystal oscillator 202 and drive circuit 204.

Figure 11:
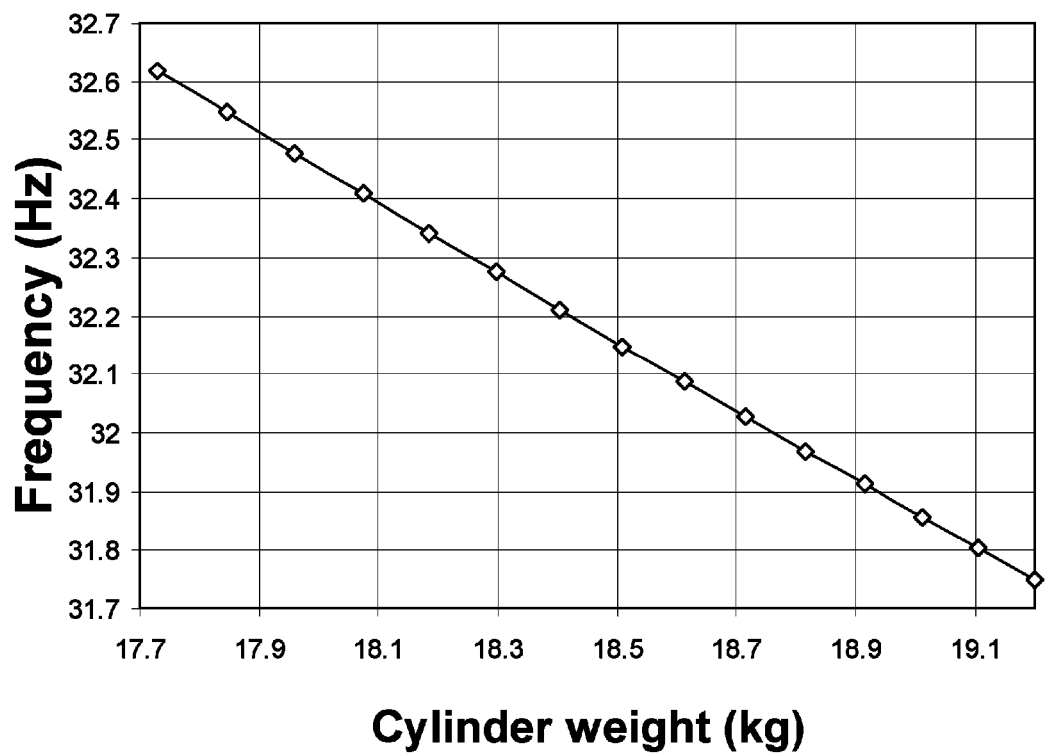
FIG. 11 shows a graph of frequency (in kHz) on the Y-axis as a function of gas cylinder mass (in kg) on the X-axis for a typical gas cylinder.

FIG. 11 illustrates further experimental data showing the operation of the present invention. FIG. 11 shows a graph of frequency (in kHz) on the Y-axis as a function of total cylinder mass (in kg) on the X-axis. As can be seen, the graph is, to a high degree of accuracy, approximately linear. Therefore, FIG. 11 shows that the mass of gas within the gas cylinder 100 can be measured accurately with the quartz crystal oscillator 202.

Figure 12:
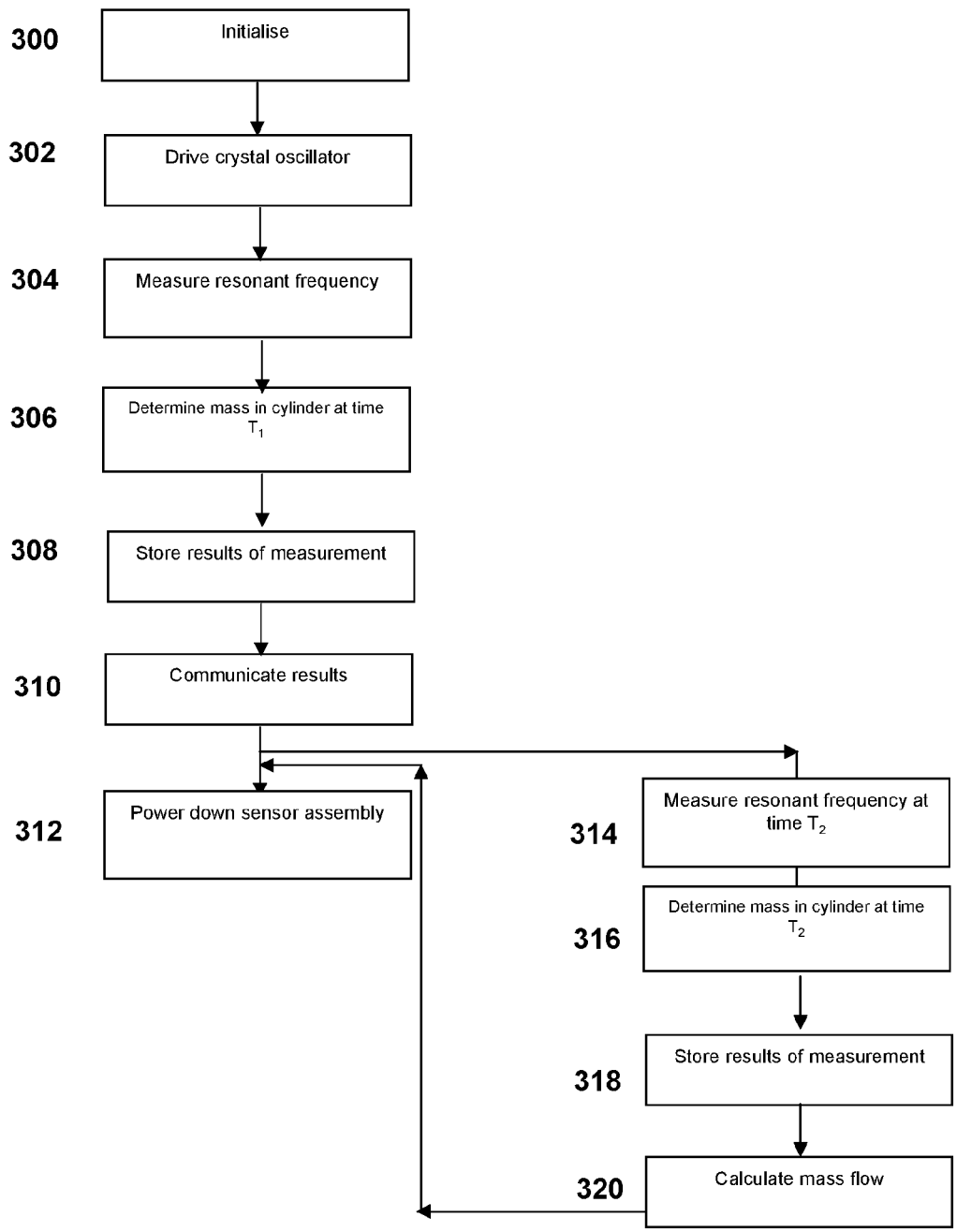
FIG. 12 is a flow chart illustrating a method according to a described embodiment.

A method according to an embodiment of the present invention will now be described with reference to FIG. 12. The method described below is applicable both of the first and second embodiments described above with reference to FIGS. 2 and 3.

Step 300: Initialise Measurement

At step 300, the measurement of the mass of gas in the gas cylinder 100 is initialised. This may be activated by, for example, a user pressing a button on the outside of the gas cylinder 100. Alternatively, the measurement may be initiated by means of a remote connection, for example, a signal transmitted across a wireless network and received by the sensor assembly 200 through the antenna 250 (see FIG. 3).

As a further alternative or addition, the sensor assembly 200 may be configured to initialise remotely or on a timer. The method proceeds to step 302.

Step 302: Drive the Quartz Crystal Oscillator

Once initialised, the drive circuit 204 is used to drive the quartz crystal oscillator 202. During initialisation, the drive circuit 204 applies a random noise AC voltage across the crystal 202. At least a portion of that random voltage will be at a suitable frequency to cause the crystal 202 to oscillate. The crystal 202 will then begin to oscillate in synchrony with that signal.

By means of the piezoelectric effect, the motion of the quartz crystal oscillator 202 will then generate a voltage in the resonant frequency band of the quartz crystal oscillator 202. The drive circuit 204 then amplifies the signal generated by the quartz crystal oscillator 202, such that the signals generated in the frequency band of the quartz crystal resonator 202 dominate the output of the drive circuit 204. The narrow resonance band of the quartz crystal filters out all the unwanted frequencies and the drive circuit 204 then drives the quartz crystal oscillator 202 at the fundamental resonant frequency f Once the quartz crystal oscillator 202 has stabilised at a particular resonant frequency, the method proceeds to step 304.

Step 304: Measure Resonant Frequency of Quartz Crystal Oscillator

The resonant frequency f is dependent upon the conditions within the internal volume V of the gas cylinder. In the present embodiment, the change in resonant frequency Δf is proportional in magnitude to the change in density of gas within the gas cylinder 100 and will decrease with increasing density.

In order to make a measurement, the frequency of the quartz crystal oscillator 202 is measured for a period of approximately 1 s. This is to enable the reading to stabilise and for sufficient oscillations to be counted in order to determine an accurate measurement. The measurement of frequency is carried out in the processor 220. The processor 220 may also log the time, $T_1$, when the measurement was started.

Once the frequency has been measured, the method proceeds to step 306.

Step 306: Determine Mass of Gas in Gas Cylinder

Once the frequency of the quartz crystal oscillator 202 has been measured satisfactorily in step 303, the processor 220 then calculates the mass of gas in the gas cylinder 100.

This is done using equation 5) above where the mass of the gas can be calculated directly from the density determined in step 304 and the known internal volume V of the gas cylinder 100. The method then proceeds to step 308.

Step 308: Store Results of Measurement

Once the mass of gas has been calculated, the mass could be simply recorded in an internal memory associated with the processor 220 of the sensor assembly 200 for later retrieval. As a yet further alternative, the mass of gas at time $T_1$ could be stored in a memory local to said processor 220.

The method then proceeds to step 310.

Step 310: Communicate Results

As an optional step, the mass of gas can be displayed in a number of ways. For example, a screen attached to the gas cylinder 100 or valve 104 could display the mass of gas contained within the gas cylinder 100. In the alternative, the mass of gas measurement could be communicated remotely to a base station or to a meter located on an adjacent fitting.

The method then proceeds to step 312.

Step 312: Power Down Sensor Assembly

It is not necessary to keep the sensor assembly 200 operational at all times. To the contrary, it is beneficial to reduce power consumption by switching the sensor assembly 200 off when not in use. This prolongs the life of the battery 206.

The configuration of the drive circuit 204 enables the quartz crystal oscillator 202 to be restarted irrespective of the gas pressure in the gas cylinder 100. Therefore, the sensor assembly 200 can be shut down as and when required in order to save battery power.

The method of operation of an embodiment of the present invention has been described above with reference to step 300 to 310 above. However, the following additional steps may also optionally be made:

Steps 314-318: Make Further Determination of Mass

It may be desired to calculate the mass flow of gas to/from the gas cylinder 100. At a time $T_2$ which is later than $T_1$, steps 314, 316 and 318 are carried out. Steps 314, 316 and 318 correspond to steps 304, 306 and 308 respectively carried out at time $T_2$. The resulting values from steps 314, 316 and 318 are stored in the internal memory of the processor 220 as a mass of gas at time $T_2$.

The time interval between $T_1$ and $T_2$ may be very short, of the order of seconds as illustrated by FIG. 9. Alternatively, if the flow rate is slow, or if it is desired to measure losses within the gas cylinder 100 due to, for example, leaks, then the time interval between $T_1$ and $T_2$ may be considerably greater; for example, of the order of minutes, hours or days.

The method then proceeds to step 320.

Step 320: Calculate Mass Flow

Knowing the time difference between times $T_1$ and $T_2$, and the mass of gas in the gas cylinder 100 at those times, the processor 220 can calculate the mass flow in the period of time between $T_1$ and $T_2$ from equation 6).

The method can then perform repeat steps 314 to 320 to calculate further mass flow if required. Alternatively, the method can move to step 312 and the sensor assembly 200 can be powered down.

Variations of the above embodiments will be apparent to the skilled person. The precise configuration of hardware and software components may differ and still fall within the scope of the present invention. The skilled person would be readily aware of alternative configurations which could be used.

Figure 13:
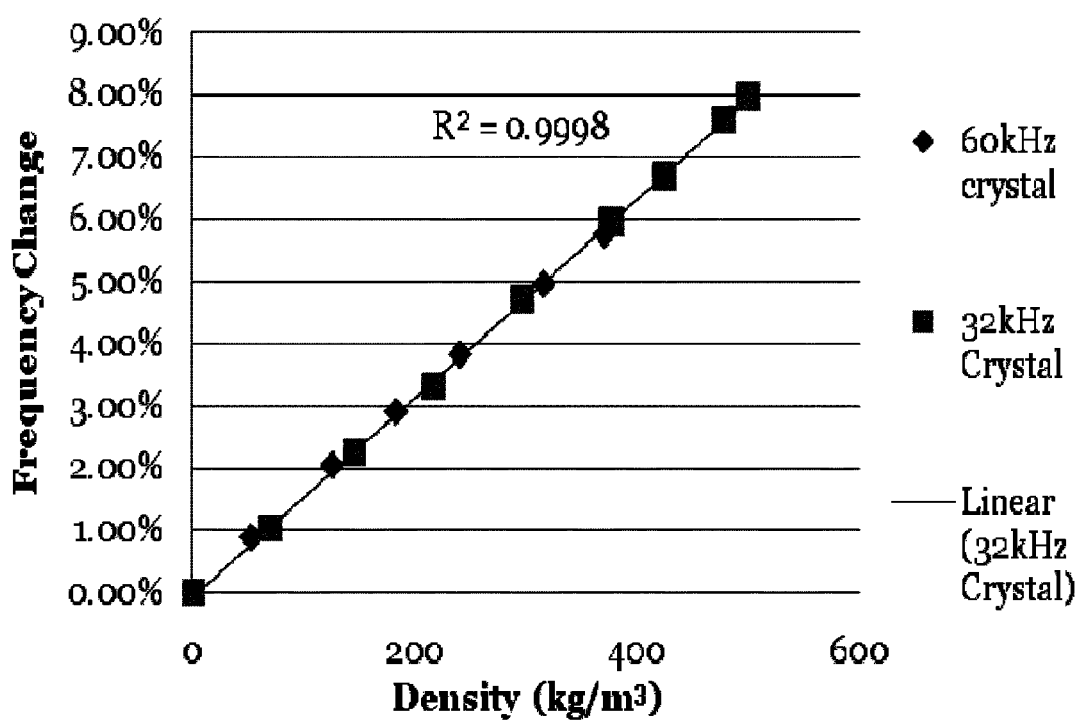
FIG. 13 shows a graph of the frequency behaviour of different crystal types.

For example, the above described embodiments have utilised a quartz crystal oscillator having a fundamental frequency of 32.768 kHz. However, crystals operating at alternative frequencies may be used. For example, quartz crystal oscillators operating at 60 kHz and 100 kHz may be used with the embodiments described above. A graph showing the frequency change with density for different crystals is shown in FIG. 13. As a further example, a crystal oscillator operating at a frequency of 1.8 MHz could be used.

Higher frequency operation enables the pressure to be monitored more frequently because a shorter time period is required to sample a given number of cycles. Additionally, higher frequency crystals enable a smaller duty cycle to be used in a "sleep" mode of a crystal. By way of explanation, in most cases, the crystal and drive circuit will spend most of the time switched off, only being switched on for a second or so when a measurement is needed. This may occur, for example, once a minute. When a higher frequency crystal is used, the pressure can be measured faster. Therefore, the time in which the crystal is operational can be reduced. This may reduce power consumption and concomitantly improve battery life.

Additionally, the above embodiments have been described by measuring the absolute frequency of a quartz crystal oscillator. However, in self-contained electronics incorporated in a gas cylinder associated regulator, it may advantageous to measure the shift in frequency of the sensor by comparing that frequency with a reference crystal of identical type but enclosed in a vacuum or pressure package. The pressure package may contain gas at a selected density, gas under atmospheric conditions or may be open to the atmosphere external of the gas cylinder 100.

Figure 14:
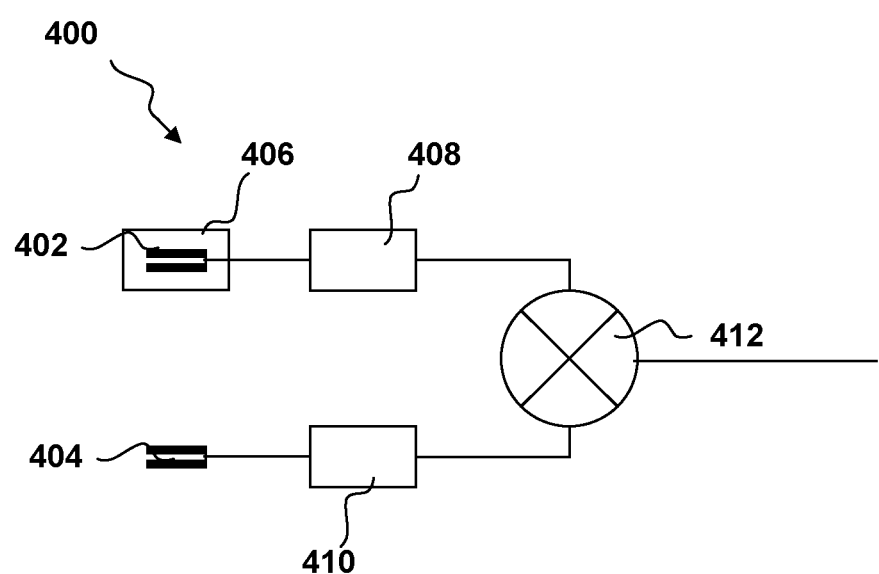
FIG. 14 is a schematic diagram showing an alternative sensor assembly comprising two quartz crystals.

A suitable sensor assembly 400 is shown in FIG. 14. The sensor assembly 400 comprises a first quartz crystal oscillator 402 and a second quartz crystal oscillator 404. The first quartz crystal oscillator 402 is a reference crystal which is located within a sealed container 406 under vacuum. The first quartz crystal oscillator 402 is driven by a drive circuit 408.

The second quartz crystal oscillator 404 is a crystal similar to the crystal 202 described in the earlier embodiments. The second quartz crystal oscillator 404 is exposed to the gas environment within the internal volume of the gas cylinder 100. The second quartz crystal oscillator 404 is driven by a drive circuit 410.

This comparison may be performed using an electronic mixer circuit 412 which combines the two frequency signal and produces an output at a frequency equal to the difference between the two crystals. This arrangement enables small changes due to, for example, temperature to be negated.

Further, the circuitry used in a gas cylinder 100 can be simplified because only the difference frequency is required to be measured. Further, this approach is particularly suitable for use with a high frequency (MHz) crystal oscillator, where it may be difficult to measure the crystal frequency directly.

Additionally, all of the electronics required to measure and display the density, mass or mass flow need not be mounted on or in the gas cylinder. For example, electronic functions could be split between units mounted on the cylinder permanently and units mounted on either a customer's usage station or temporarily mounted on the outlet of the cylinder such as the position normally used for a conventional flow meter.

Figure 15:
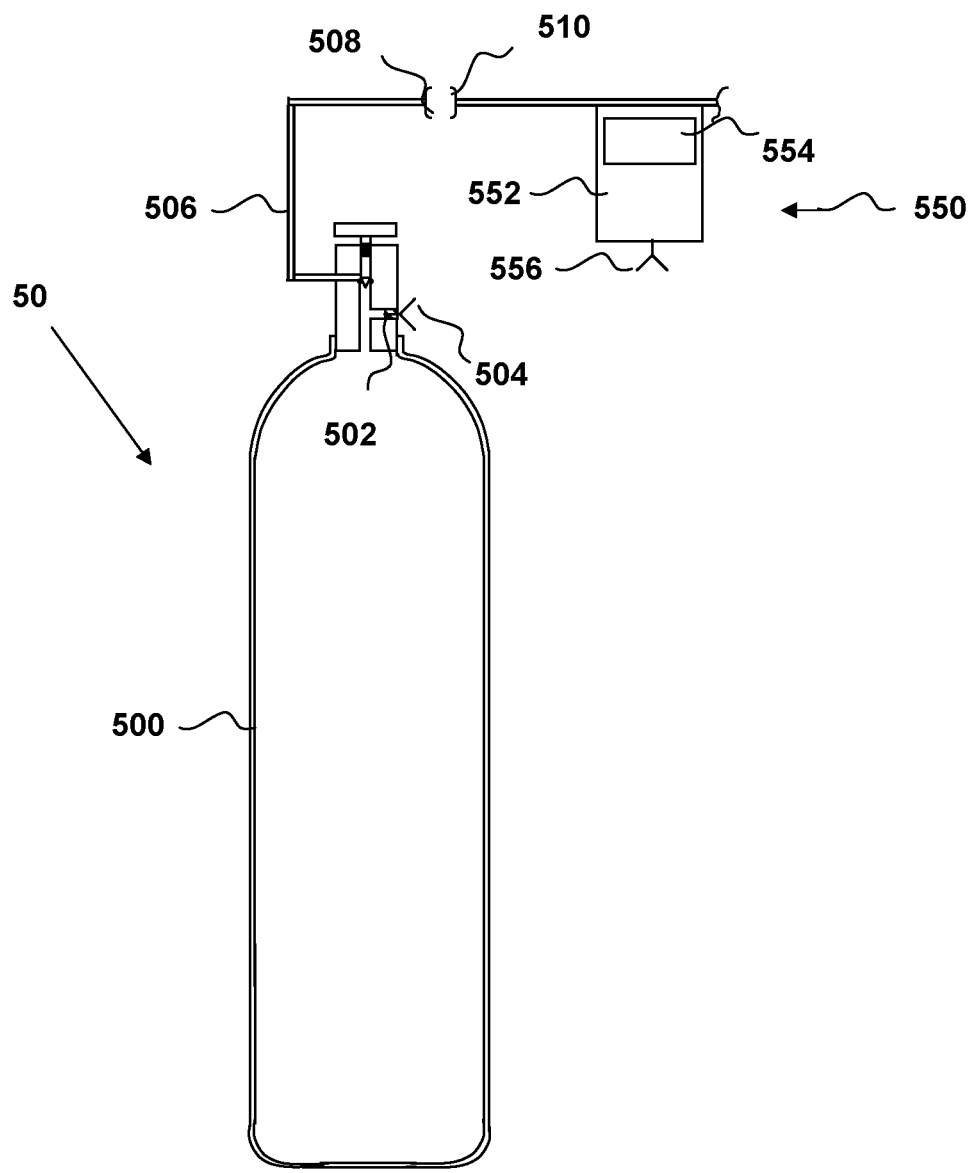
FIG. 15 shows an alternative arrangement using a remote electronic data unit.

An example of this arrangement is shown with reference to FIG. 15. The arrangement comprises a gas cylinder assembly 50 comprising a gas cylinder 500 and a sensor assembly 502. The gas cylinder assembly 50, gas cylinder 500 and sensor assembly 502 are substantially similar to the gas cylinder assembly 10, gas cylinder 100 and sensor assembly 200 substantially as previously described with reference to previous embodiments.

In this embodiment, the sensor assembly 502 comprises a quartz crystal oscillator and drive circuit (not shown) similar to the quartz crystal oscillator 202 and drive circuit 204 of earlier embodiments. An antenna 504 is provided for communication via any suitable remote communication protocol; for example, Bluetooth, Infra-red (IR) or RFID. Alternatively, one-wire communication may be utilised.

As a further alternative, acoustic communication methods may be used. The advantage of such methods is that remote communication can be effected without the requirement for an external antenna 250.

A connection pipe 506 is connected to the outlet of the gas cylinder 500. The connection pipe is terminated by a quick connect connection 508. The quick connect connection 508 enables connecting pipe work or components to be connected and disconnected easily and quickly from the gas cylinder 500.

A quick connect unit 550 is provided for connection to the gas cylinder 500. A complementary quick connect connector 510 is provided for connection to the connector 508. Further, the quick connect unit 550 is provided with a data unit 552. The data unit 552 comprises a display 554 and an antenna 556 for communication with the antenna 504 of the gas cylinder assembly 50. The display 554 may comprise, for example, an E-ink display to minimise power consumption and maximise visibility of the display.

The data unit 552 may log various parameters as measured by the sensor assembly 502 of the gas cylinder assembly 50. For example, the data unit 552 could log flow rate versus time. Such a log could be useful, for example, to welding contractors wishing to check that gas flow was present and correct during lengthy gas welding procedures on critical components, or to supply data on a particular customer's usage.

Additionally, the data obtained from the gas cylinder 500 may be used to present data on the run out time, i.e. the time before the gas in the cylinder 500 is used up. This is particularly critical in applications such as a hospital oxygen cylinder used in patient transit between hospitals. Such a time ($T_{ro}$) can be calculated from knowledge of the flow rate (discussed above), mass contents of the cylinder 500 and the current time ($T_c$) via the following equation:

$$T_{ro} = T_c + \frac{M}{\frac{\partial M}{\partial t}} \qquad 7)$$

Alternatively, data from the data unit 550 can be output to a computer-enabled welding machine (for welding applications) or other gas-using equipment, to allow the calculation of derived parameters, along with warning messages. Non-exhaustive examples of this may be: Gas used per unit arc time, gas used per kg of welding wire (eg. with warning about porosity of weld), the number of standard-size balloons (or to measure and calibrate for balloons of a non-standard size), the number of hours of welding remaining, the display of pressure (by converting the measured density value to pressure using known gas data).

Additionally, the data unit 550 may be arranged to provide the following functions: to provide an audible or visible alarm if the gas level is below a certain level or flow rate; to output the cylinder lifetime (e.g. for mixtures which change slowly) or a cylinder expiry date; to contain and display data on use of gas, i.e. which types of welding, what types of metal welded, or give links so that mobile phones or computers can pick up detailed data; to provide multimode operation, e.g. a supplier/filler mode and a customer mode; to display different quantities to the customer from that which is displayed by the gas company which refills the cylinders; to allow input of data; to provide data such as a cylinder number, the type of gas, a certificate of analysis, a customer history (who had the cylinder over what dates), safety data and operational tips can be carried in summary form on the cylinder.

As an alternative, all of the above examples may, optionally, be processed, stored or obtained from a system located entirely on (or within) the gas cylinder 500 as discussed in terms of the sensor assembly 200, 502.

Additionally, the embodiments of the present invention may also be used to perform leak detection. A quartz crystal oscillator is particularly suitable to this task due to the great sensitivity of such a sensor. Additionally, a quartz crystal oscillator will not incorrectly read pressure changes due to changes in the temperature of the cylinder, as is the case when sensing leaks using a pressure gauge. Additionally, embodiments of the invention can be used to detect failures, for example, in detection of residual pressure valve failure (e.g. in a used cylinder with pressure below 3 bar g)

Whilst the above embodiments have been described with reference to the use of a quartz crystal oscillator, the skilled person would be readily aware of alternative piezoelectric materials which could also be used. For example, a non-exhaustive list may include crystal oscillators comprising: lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, or dipotassium tartrate.

Additionally, whilst the above embodiments have been illustrated with reference to gas cylinders, other applications of the present invention may be utilised. For example, the quartz crystal oscillator may be located within the tyre of a vehicle such as a car, a motorbike or a truck. Whilst the shape of the tyre of a vehicle may change under load or at speed, the inventors of the present application have shown that the internal volume of the tyre does not change significantly in use. For example, provided that the change in internal volume is, in this context, less than 2-3% of the total internal volume, the present invention is reliably operable to calculate the mass of gas within a tyre of the vehicle.

Further, whilst many applications use air as the gas within a vehicle tyre, increasingly, gases such as Nitrogen are used. The arrangements of the present invention are particularly suitable to such applications. Further, because the measurement of mass is essentially independent of temperature, the arrangement of the present invention is particularly useful in situations where environmental conditions may affect measurements.

As a further example, the present invention may also be applicable to air suspension systems for vehicles.

Embodiments of the present invention have been described with particular reference to the examples illustrated. While specific examples are shown in the drawings and are herein described in detail, it should be understood, however, that the drawings and detailed description are not intended to limit the invention to the particular form disclosed. It will be appreciated that variations and modifications may be made to the examples described within the scope of the present invention.

The invention claimed is:

1. A method of measuring the mass of a gas under pressure using a piezoelectric oscillator, said gas being contained within a gas cylinder having a fixed internal volume (V), the method comprising:
   a) immersing a tuning fork piezoelectric oscillator in the gas within the gas cylinder;
   b) driving the piezoelectric oscillator at a resonant oscillation frequency;
   c) measuring the oscillation frequency of the piezoelectric oscillator to measure the density of the gas within the gas cylinder;
   d) determining, from the density measurement and from the internal volume (V) of said gas cylinder, the mass of the gas within the gas cylinder.

2. A method according to claim 1, wherein step b) comprises:
   driving the piezoelectric oscillator by a drive circuit powered by a battery
   cyclically alternating between switching the drive circuit on and off to conserve battery power; and
   wherein step c) comprises: measuring said resonant frequency over a pre-determined time period when the drive circuit is switched on to determine the density of gas in said gas cylinder.

3. A method according to claim 1, wherein steps b) through d) are repeated one or more times such that a series of measurements of the gas density within the gas cylinder over a period of time is obtained, said series of measurements being utilized to determine the change in mass of gas within gas cylinder during said period of time.

4. A method according to claim 1, wherein said piezoelectric oscillator comprises a quartz crystal oscillator.

5. A sensor assembly for measuring the mass of a gas under pressure within a gas cylinder having a fixed internal volume (V), the sensor assembly comprising:
   a tuning fork piezoelectric oscillator mounted so as to be immersed in the gas within the gas cylinder;
   a drive circuit arranged to drive the piezoelectric oscillator at a resonant oscillation frequency, and arranged to measure the oscillation frequency of the piezoelectric oscillator in the gas; and
   a processor configured to determine, from the frequency, the density of the gas within the gas cylinder and further configured to determine, from the density measurement and from the internal volume (V) of said gas cylinder, the mass of the gas within the gas cylinder.

6. A sensor assembly according to claim 5, further comprising a drive circuit comprising a Darlington pair arranged in a feedback configuration from a common emitter amplifier.

7. A sensor assembly according to claim 5, wherein the drive circuit is powered by a battery and wherein the sensor assembly is arranged to cyclically alternate between switching the drive circuit on and off to conserve battery power and to measure said resonant oscillation frequency over a pre-determined time period when the drive circuit is switched on to determine the density of gas in said gas cylinder.

8. A sensor assembly according to claim 5, wherein the drive circuit and processor are further arranged to perform repeat measurements of the mass of the gas within the gas cylinder at discrete time intervals to obtain a plurality of measurements, and to determine, from said plurality of measurements, the mass flow of gas to/from the gas cylinder during the discrete time intervals, more times such that a series of measurements of the gas density within the gas cylinder over a period of time is obtained, said series of measurements being utilized to determine the change in mass of gas within said gas cylinder during said period of time.

9. A gas cylinder for containing a gas under pressure and having a fixed internal volume (V), wherein the sensor assembly of claim 5 is located entirely within the fixed internal volume (V) of the gas cylinder.

10. A valve arrangement comprising the sensor assembly of claim 5, the valve arrangement being for connection to a gas cylinder body to form the gas cylinder having a fixed internal volume (V), the valve arrangement being arranged to enable selective filling of the gas cylinder with gas or dispensation of gas from the gas cylinder.

11. A gas cylinder for containing a gas under pressure, the gas cylinder having a fixed internal volume (V) and comprising:
   a gas cylinder body defining a fixed internal volume (V);
   a valve arrangement connected to said gas cylinder body and arranged to enable selective filling of the gas cylinder with gas or dispensation of gas from said gas cylinder; and
   the sensor assembly of claim 5.

* * * * *